United States Patent
Takacs et al.

(10) Patent No.: US 10,212,928 B2
(45) Date of Patent: *Feb. 26, 2019

(54) METHODS AND APPARATUS FOR ATTRACTING RATS

(71) Applicant: Scotts Canada Ltd., Toronto, Ontario (CA)

(72) Inventors: Stephen J. Takacs, Burnaby (CA); Antonia E. Musso, Burnaby (CA); Regine M. Gries, Coquitlam (CA); Gerhard G. Gries, Coquitlam (CA)

(73) Assignee: SCOTTS CANADA LTD., Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/882,704

(22) Filed: Jan. 29, 2018

(65) Prior Publication Data

US 2018/0249700 A1    Sep. 6, 2018

Related U.S. Application Data

(62) Division of application No. 14/402,752, filed as application No. PCT/CA2013/050397 on May 24, 2013, now Pat. No. 9,877,471.

(Continued)

(51) Int. Cl.
*A01M 29/06* (2011.01)
*A01M 29/16* (2011.01)
(Continued)

(52) U.S. Cl.
CPC ............ *A01M 29/16* (2013.01); *A01M 23/00* (2013.01); *A01M 23/16* (2013.01);
(Continued)

(58) Field of Classification Search
CPC ...... A01M 29/06; A01M 29/18; A01M 99/00; A01N 25/004
See application file for complete search history.

(56) References Cited

U.S. PATENT DOCUMENTS

| 4,105,992 A | 8/1978 | Luciano |
| 2005/0181003 A1 | 8/2005 | Endepols |

FOREIGN PATENT DOCUMENTS

| CN | 201967568 U | 9/2011 |
| DE | 10326833 A1 | 2/2005 |

(Continued)

OTHER PUBLICATIONS

"Rats and Mice: What's the Difference". ratbehaviororg, 2010. Web May 4, 2016. http://web.archive.org/web/20100525165650/http://www.ratbehavior.org/RatsMice.htm.

*Primary Examiner* — Christopher P Ellis
(74) *Attorney, Agent, or Firm* — Ulmer & Berne LLP

(57) ABSTRACT

An acoustic signal for attracting rats comprising a playback recording or synthetic generation of vocalizations of rats or mice is provided. The vocalizations may be of rat pups, and may be characterized by sonic frequency components in the range of 1.8-7.5 kHz and/or ultrasonic frequency components in the ranges of 21-24 kHz, 40-50 kHz and/or 60-96 kHz. The vocalizations may be of adult male rats, including courting adult male rats, characterized by sonic frequency components in the range of 15-20 kHz and/or ultrasonic frequency components in the range of 20-100 kHz. The vocalizations may be of adult female mice, including nursing adult female mice, characterized by sonic frequency components in the range of 8-12 kHz and/or ultrasonic frequency components in the range of 25-100 kHz.

20 Claims, 13 Drawing Sheets

Related U.S. Application Data

(60) Provisional application No. 61/826,432, filed on May 22, 2013, provisional application No. 61/651,388, filed on May 24, 2012.

(51) Int. Cl.
*A01M 23/16* (2006.01)
*A01M 29/18* (2011.01)
*A01N 25/00* (2006.01)
*A01M 23/00* (2006.01)
*A01M 25/00* (2006.01)
*A01M 99/00* (2006.01)

(52) U.S. Cl.
CPC .......... *A01M 25/004* (2013.01); *A01M 29/18* (2013.01); *A01M 99/00* (2013.01); *A01N 25/004* (2013.01)

(56) References Cited

FOREIGN PATENT DOCUMENTS

| | | |
|---|---|---|
| EP | 1279334 B1 | 1/2003 |
| SU | 1724148 A1 | 4/1992 |
| WO | 96003037 A1 | 2/1996 |
| WO | 2013003946 A1 | 1/2013 |

US 10,212,928 B2

METHODS AND APPARATUS FOR ATTRACTING RATS

RELATED APPLICATIONS

This application is a divisional of U.S. Non-Provisional patent application Ser. No. 14/402,752 filed Nov. 21, 2014, which is a U.S. National Stage Entry that claims priority to PCT patent application no. PCT/CA2013/050397 filed May 24, 2013, which claims priority to U.S. provisional application No. 61/826,432 filed May 22, 2013, and U.S. provisional application No. 61/651,388 filed May 24, 2012.

FIELD OF THE INVENTION

The invention relates generally to methods and apparatus for attracting rats.

BACKGROUND OF THE INVENTION

Rats damage crops and stored foodstuffs, and also cause harm by vectoring diseases like Bubonic plague. Chemical attractants are known to be useful in luring rats to traps and rodenticides. Improved methods and apparatus for attracting rats are desirable.

SUMMARY OF THE INVENTION

According to one aspect, an acoustic signal for attracting rats comprising a playback recording or synthetic generation of vocalizations of rats or mice is provided. The vocalizations may be of rat pups, and may be characterized by sonic frequency components in the range of 1.8-7.5 kHz and/or ultrasonic frequency components in the ranges of 21-24 kHz, 40-50 kHz and/or 60-96 kHz. The vocalizations may be of adult male rats, including courting adult male rats, characterized by sonic frequency components in the range of 15-20 kHz and/or ultrasonic frequency components in the range of 20-100 kHz. The vocalizations may be of adult female mice, including nursing adult female mice, characterized by sonic frequency components in the range of 8-12 kHz and/or ultrasonic frequency components in the range of 25-100 kHz.

The vocalizing species of rat may be selected from the group consisting of *Rattus norvegicus, Rattus rattus, Rattus annandalei, Rattus enganus, Rattus everetti, Rattus exulans, Rattus hainaldi, Rattus hoogerwerfi, Rattus korinchi, Rattus macleari, Rattus montanus, Rawls morotaiensis, Rattus nativiiatis, Rattus ranjiniae, Rattus sanila, Rawls stoicus, Rattus timorensis, Rattus nitidus, Rattus pyctoris, Rattus turkestanicus, Rattus adustus, Rattus andamanensis, Rattus argentiventer, Rattus baluensis, Rattus blangorum, Rattus burrus, Rattus hoffmanni, Rattus koopmani, Rattus losea, Rattus lugens, Rattus mindorensis, Rattus mollicomulus, Rattus osgoodi, Rattus palmarum, Rattus rattus, Rattus satarae, Rattus simalurensis, Rattus tanezumi, Rattus tawitawiensis, Rattus tiomanicus, Rattus bontanus, Rattus foramineus, Rattus martnosurus, Rattus pelurus, Rattus salocco, Rattus xanthurus, Rattus arfakiensis, Rattus arrogans, Rattus elaphinus, Rattus feliceus, Rattus giluwensis, Rattus jobiensis, Rattus leucopus, Rattus mordax, Rattus niobe, Rattus novaeguineae, Rattus omichlodes, Rattus pococki, Rattus praetor, Rattus richardsoni, Rattus steini, Rattus vandeuseni, Rattus verecundus, Rattus colletti, Rattus fuscipes, Rattus lutreolus, Rattus sordidus, Rattus tunneyi, and Rattus villosissimus.*

The vocalizing species of mice may be *Mus musculus.*

The attracted rats may be selected from the group consisting of *Rattus norvegicus, Rattus rattus, Rattus annandalei, Rattus enganus, Rattus everetti, Rattus exulans, Rattus hainaldi, Rattus hoogerwerfi, Rattus korinchi, Rattus macleari, Rattus montanus, Rattus morotaiensis, Rattus nativitatis, Rattus ranjiniae, Rattus sanila, Rattus stoicus, Rattus timorensis, Rattus nitidus, Rattus pyctoris, Rattus turkestanicus, Rattus adustus, Rattus andamanensis, Rattus argentiventer, Rattus baluensis, Rattus blangorum, Rattus burrus, Rattus hoffmanni, Rattus koopmani, Rattus losea, Rattus lugens, Rattus mindorensis, Rattus mollicomulus, Rattus osgoodi, Rattus palmarum, Rattus rattus, Rattus satarae, Rattus simalurensis, Rattus tanezumi, Rattus tawitawiensis, Rattus tiomanicus, Rattus bontanus, Rattus foramineus, Rattus marmosurus, Rattus pelurus, Rattus salocco, Rattus xanthurus, Rattus arfakiensis, Rattus arrogans, Rattus elaphinus, Rattus feliceus, Rattus giluwensis, Rattus jobiensis, Rattus leucopus, Rattus mordax, Rattus niobe, Rattus novaeguineae, Rattus omichlodes, Rattus pococki, Rattus praetor, Rattus richardsoni, Rawls sleini, Ramis vandeuseni, Rattus verecundus, Ramis colleta, Rattus fuscipes, Rattus lutreolus, Rattus sordidus, Rattus tunneyi, and Rattus villosissimus.*

The signal may comprise a playback recording of the vocalizations. Alternatively, the signal may comprise a synthetic generation of the vocalizations.

According to another aspect, a method of attracting rats is provided. The method includes the steps of (a) placing a device capable of producing acoustic signals in an area determined to have a need for capturing and/or killing rats; and (b) causing the device to emit an acoustic signal as described herein. The device may include a processor programmed to generate the acoustic signal. The processor may include an electronically activatable microchip. In step (a), the device may be contained in, placed adjacent to, or integrated with a trap that captures attracted rats. In step (a) the device may be placed in an area where attracted rats will be exposed to a rodenticide. Step (b) may include modulating one or more of the frequency, duration and intensity of the acoustic signal. Step (b) may include providing intermittent silences between the acoustic signals. The durations of the intermittent silences may be altered.

Step (a) may further include placing in the area a chemical stimulus to enhance the attraction of rats. The chemical stimulus may include one or more stimuli selected from the group consisting of 2-hydroxy-3-methylcyclopent-2-en-1-one, butyric acid, 2,3-butadione, 3-methylbutanal, 5-methyl-(E)-2-hepten-4-one, γ-octalactone, 4-hydroxy-2,5-dimethylfuran-3-one, 6-methyl-4-heptanone, dimethyltrisulfide, nonanoic acid, decanoic (capric) acid, dodecanoic (lauric) acid, tetradecanoic (myristic) acid, hexadecanoic (palmitic) acid, (Z)-octadec-9-enoic (oleic) acid, octadecanoic (stearic) acid, lactic acid, glycerol, lard and cracklings, oat flour, rice flour, wheat bran, fructose, soy lecithin, safflower oil, salmon oil, and compounds derived from bedding contaminated by the urine and feces of female mice and/or rats.

The chemical stimulus may include 2-hydroxy-3-methylcyclopent-2-en-1-one, butyric acid, 2,3-butadione, 3-methylbutanal, 5-methyl-(E)-2-hepten-4-one, and γ-octalactone. The chemical stimulus may further include lard and cracklings, or a heat-treated, cereal-based composition. The cereal-based composition may include a cereal flour, a cereal bran, a gelling agent, sugar, an oil, an emulsifier and a humectant. The cereal flour may be oat flour and rice flour. The cereal bran may be wheat bran. The gelling agent may be gelatin or agar. The sugar may be fructose. The oil may be safflower oil or salmon oil. The emulsifier may be soy lecithin. The humectant may be carrageenan gum powder. The cereal-based composition may also include a preservative, such as calcium propionate. The cereal-based composition may also include dimethyltrisulfide.

According to another aspect, a method of making a lure for attracting rats is provided. The method includes the step of constructing a processor programmed to generate an acoustic signal as described herein.

According to another aspect, an apparatus including a processor programmed to generate an acoustic signal as described herein is provided. The processor may include an electronically activatable microchip.

According to another aspect, an apparatus for attracting rats is provided. The apparatus includes (a) a processor programmed to generate an acoustic signal as described herein, (b) an amplifier for amplifying the acoustic signal; and (c) a speaker for emitting the amplified acoustic signal. The processor may include an electronically activatable microchip.

DRAWINGS

Exemplary embodiments are illustrated in referenced figures of the drawings. It is intended that the embodiments and figures disclosed herein are to be considered illustrative rather than restrictive.

FIG. 1(a-c) illustrates analyses of waveform (A1, A2, A3), frequency (B1, B2, B3) and time-frequency sound intensity (sonogram) (C1, C2, C3) of representative sounds produced by a single Norway rat pup, *Rattus norvegicus*. The darker shades in C1, C2, and C3 indicate more intense frequency components. A1 inset shows a close-up view of the waveform presented in A1.

Figure 4:
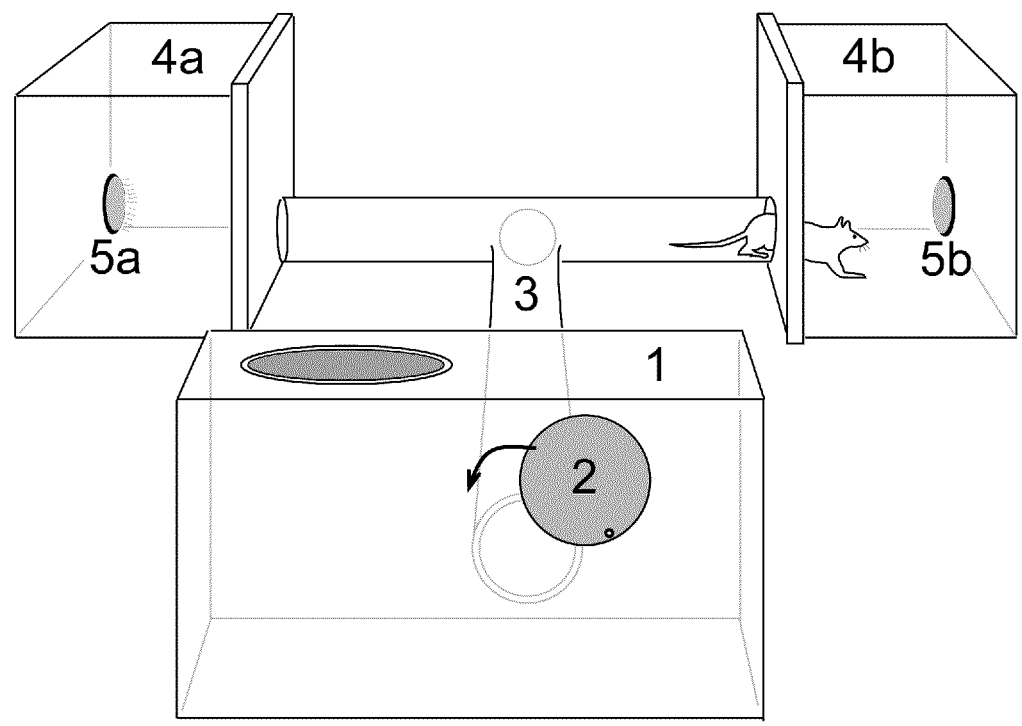

FIG. 4 illustrates the experimental design used to test behavioral responses of adult, sub-adult and juvenile male and female rats to played back recordings of vocalizations from isolated, single Norway rat pups, *Rattus norvegicus*. Numbers refer to components of the experimental design, as follows: (1) aquarium (30×30×60 cm) for housing a test rat prior to the onset of a bioassay; (2) aluminum gate with opening mechanism; (3) T-tube (75×50×10 cm); (4a, 4b) aquaria (30×30×60 cm each) housing a piezoelectric or Sennheiser 70 headphone speaker (5) emitting test stimulus.

Figure 1:
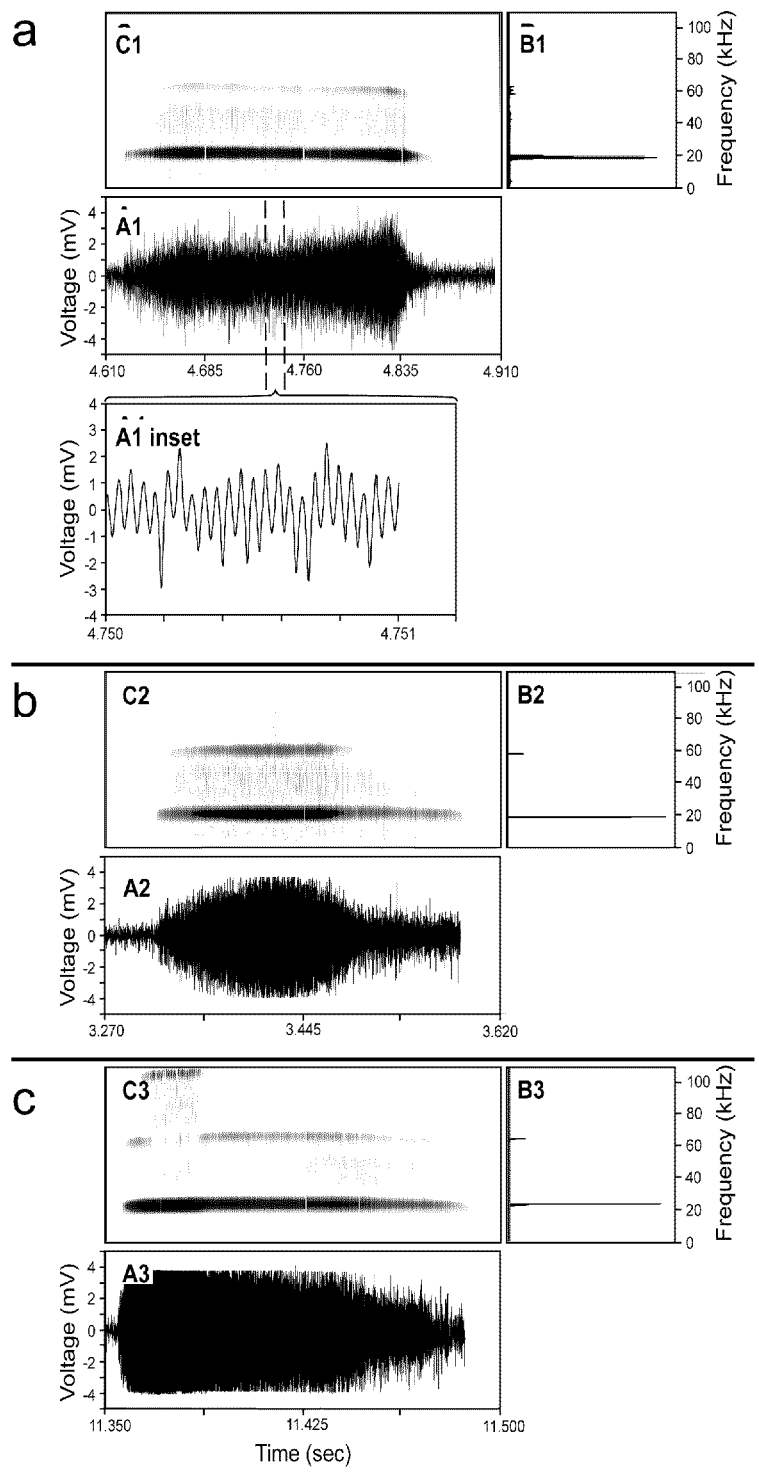
Figure 2:
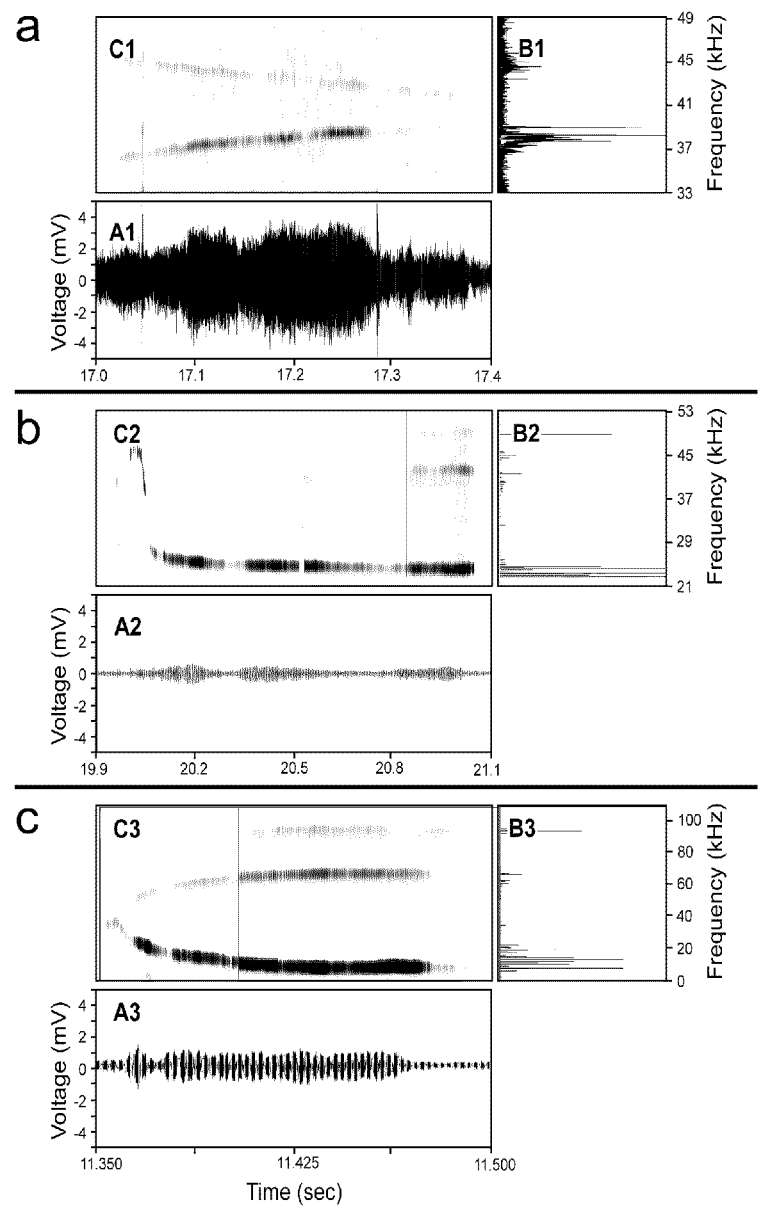
FIG. 2(a-c) illustrate the analyses of waveform (A1, A2, A3), frequency (B1, B2, B3) and time-frequency sound intensity (sonogram) (C1, C2, C3) of representative sounds produced by courting male Norway rats, *Rattus norvegicus*. The darker shades in C1, C2, and C3 indicate more intense frequency components.
Figure 5:
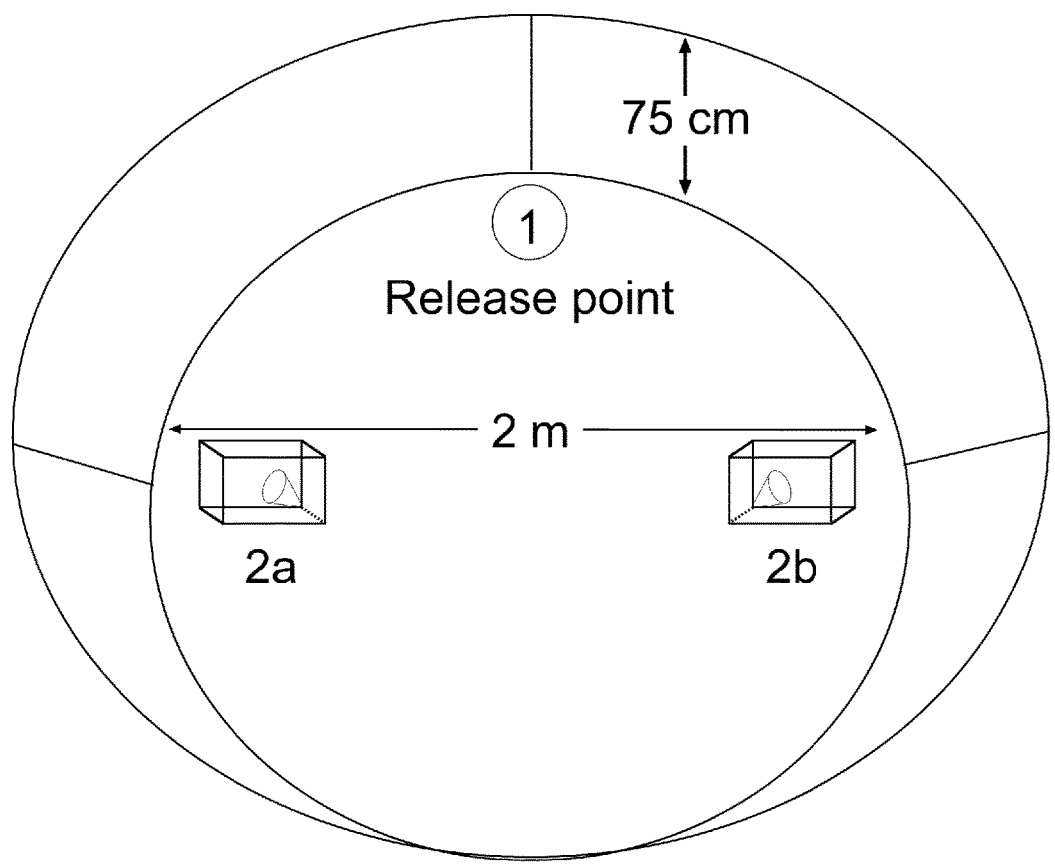

FIG. 5 illustrates the experimental design used to test behavioral responses of adult male and female Norway rats, *Rattus norvegicus*, to sonic and ultrasonic vocalizations emitted by rat pups or adult house mice, *Mus musculus* (see FIGS. 1 and 3), or to playback recordings of vocalizations from courting and mating male adult Norway rats, *Rattus norvegicus* (see FIG. 2). Numbers refer to components of the experimental design, as follows: (1) stainless steel bowl for transfer of a rat to the bioassay arena; (2a, 2b) Stainless steel bait boxes (20×20×120 cm each) housing a 1-g food bait and a piezoelectric speaker emitting test stimulus.

Figure 6:
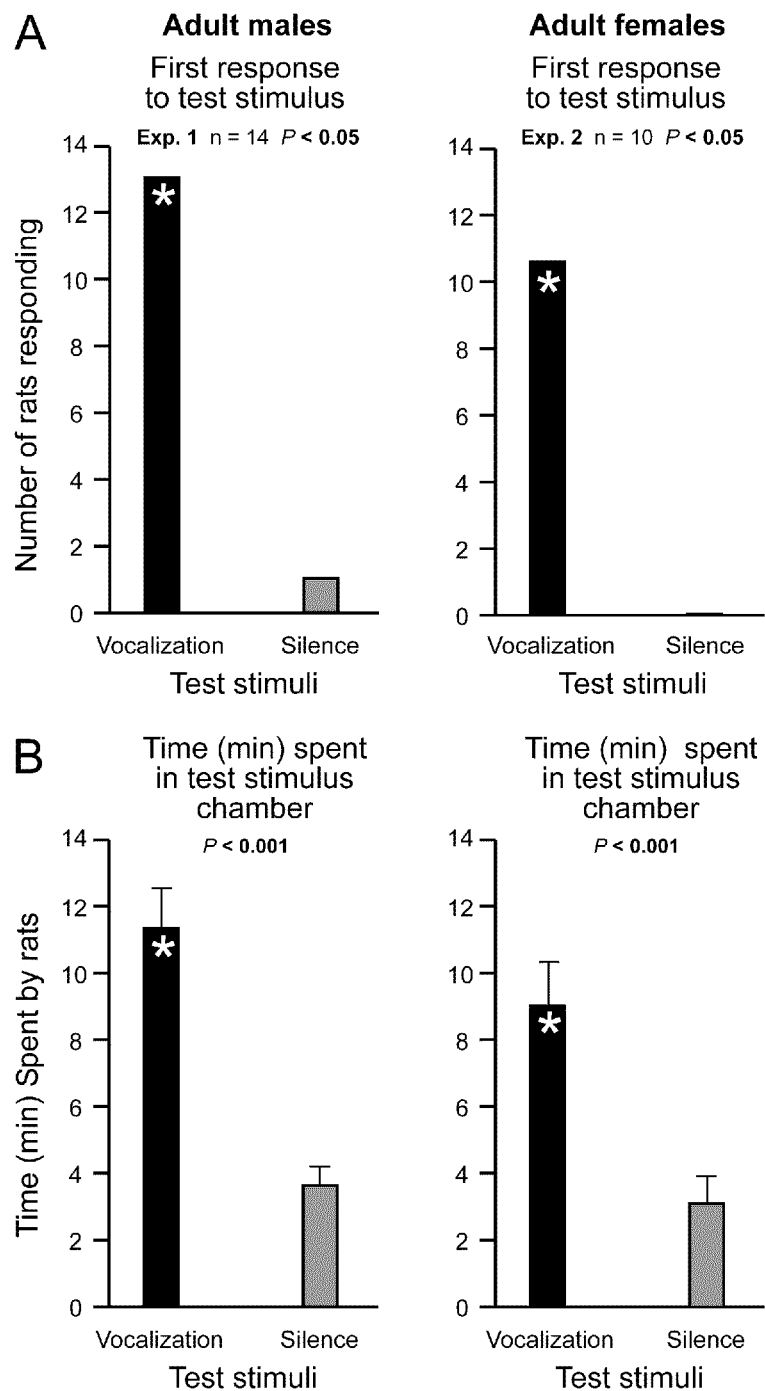

FIG. 6 illustrates (A) the first choice and (B) time spent in aquarium 4a or 4b (see FIG. 4) by >12-wk-old adult male (Experiment 1) or female (Experiment 2) *Rattus norvegicus* in response to playback recordings of vocalizations from pups of *R. norvegicus* (see FIG. 1). First-choice and time-spent data were analyzed using a binominal test and Student's t-test, respectively. In A or B of each experiment, bars with an asterisk (*) indicate a statistically significant preference (P<0.05) for a test stimulus.

Figure 7:
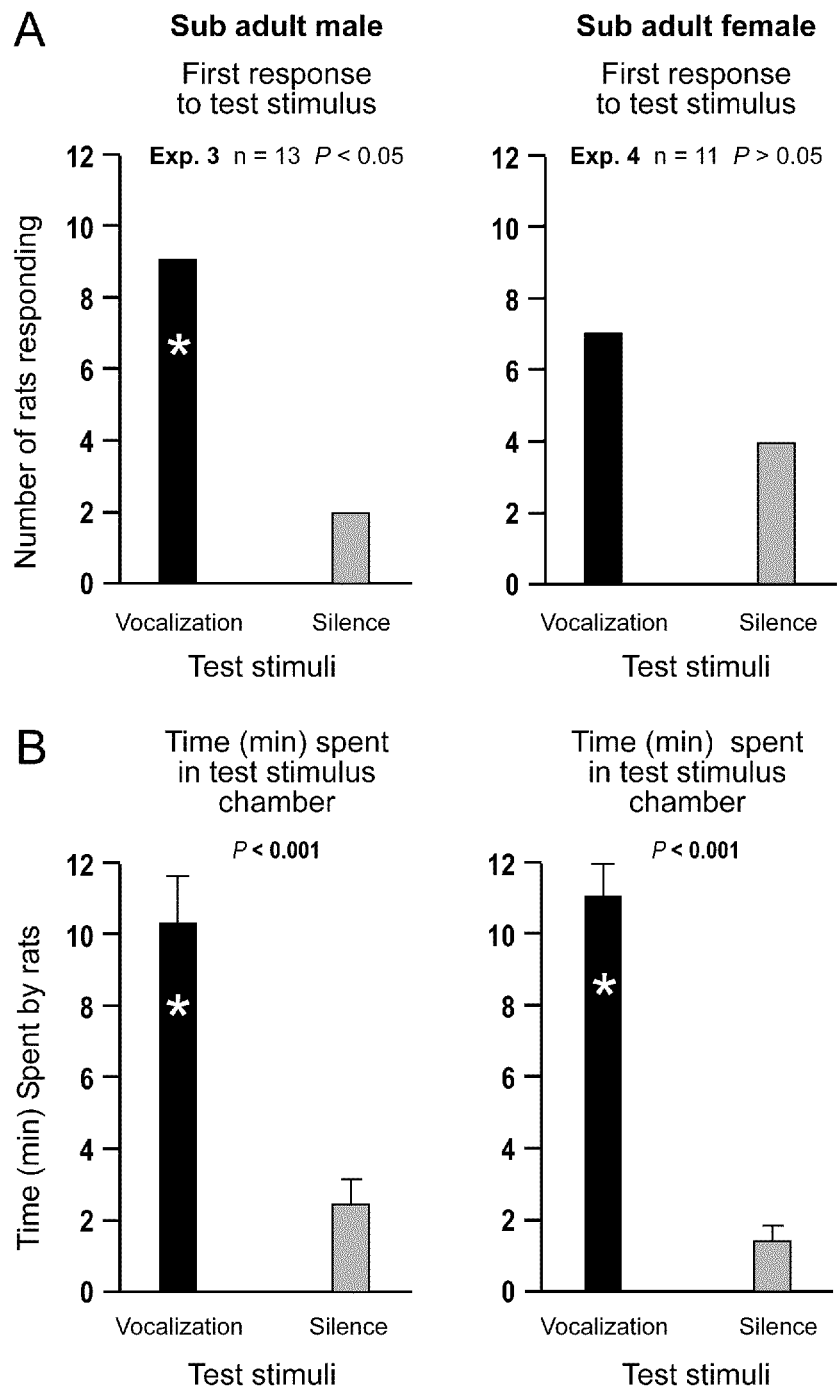

FIG. 7 illustrates (A) the first choice and (B) time spent in aquarium 4a or 4b (see FIG. 4) by 6- to 8-wk-old sub-adult male (Experiment 3) or sub-adult female (Experiment 4) *Rattus norvegicus* in response to playback recordings of vocalizations from pups of *R. norvegicus* (see FIG. 1). First-choice and time-spent data were analyzed using a binominal test and Student's t-test, respectively. In A or B of each experiment, bars with an asterisk (*) indicate a statistically significant preference (P<0.05) for a test stimulus.

Figure 8:
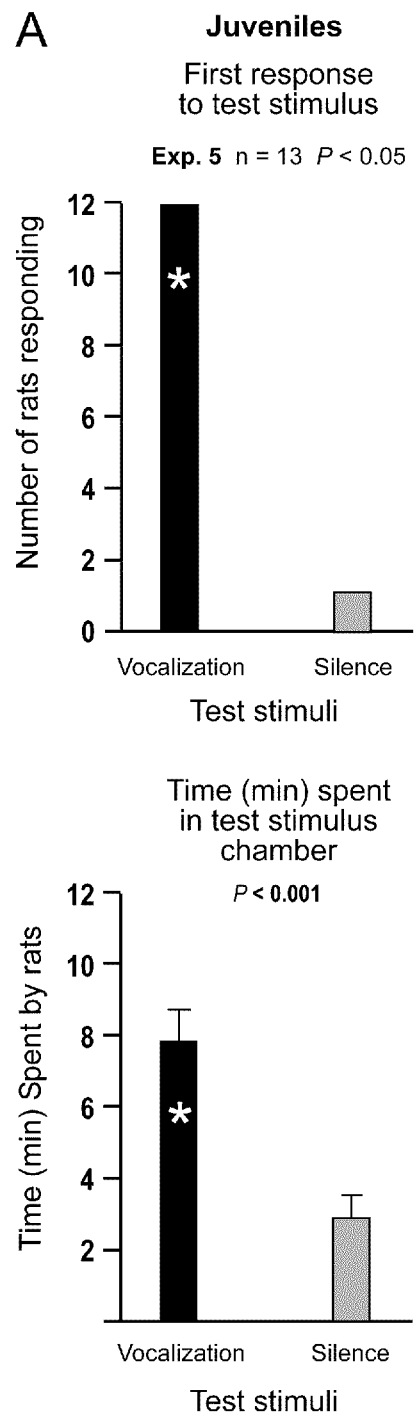

FIG. 8 illustrates (A) the first choice and (B) time spent in aquarium 4a or 4b (see FIG. 4) by 4- to 6-wk-old juveniles of *Rattus norvegicus* in Experiment 5 in response to playback recordings of vocalizations from pups of *R. norvegicus* (see FIGS. 1). First-choice and time-spent data were analyzed using a binominal test and Student's t-test, respectively. In A or B, bars with an asterisk (*) indicate a statistically significant preference (P<0.05) for a test stimulus.

Figure 9:
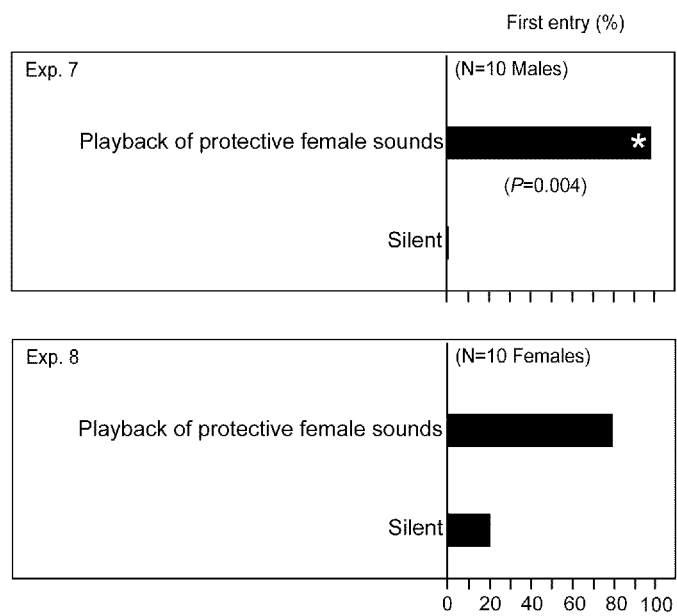

FIG. 9 illustrates the percentage of >12-wk-old adult male (Experiment 7) or >12-wk-old adult female *Rattus norvegicus* (Experiment 8) entering first a bait box (see FIG. 5) in response to computer playback of vocalizations of a nursing protective female *Mus musculus* (see FIG. 3) or in response to silence. Data were analyzed using a binominal test. In experiment 7, the bar with an asterisk (*) indicates a statistically significant preference (P<0.05) for the test stimulus.

Figure 10:
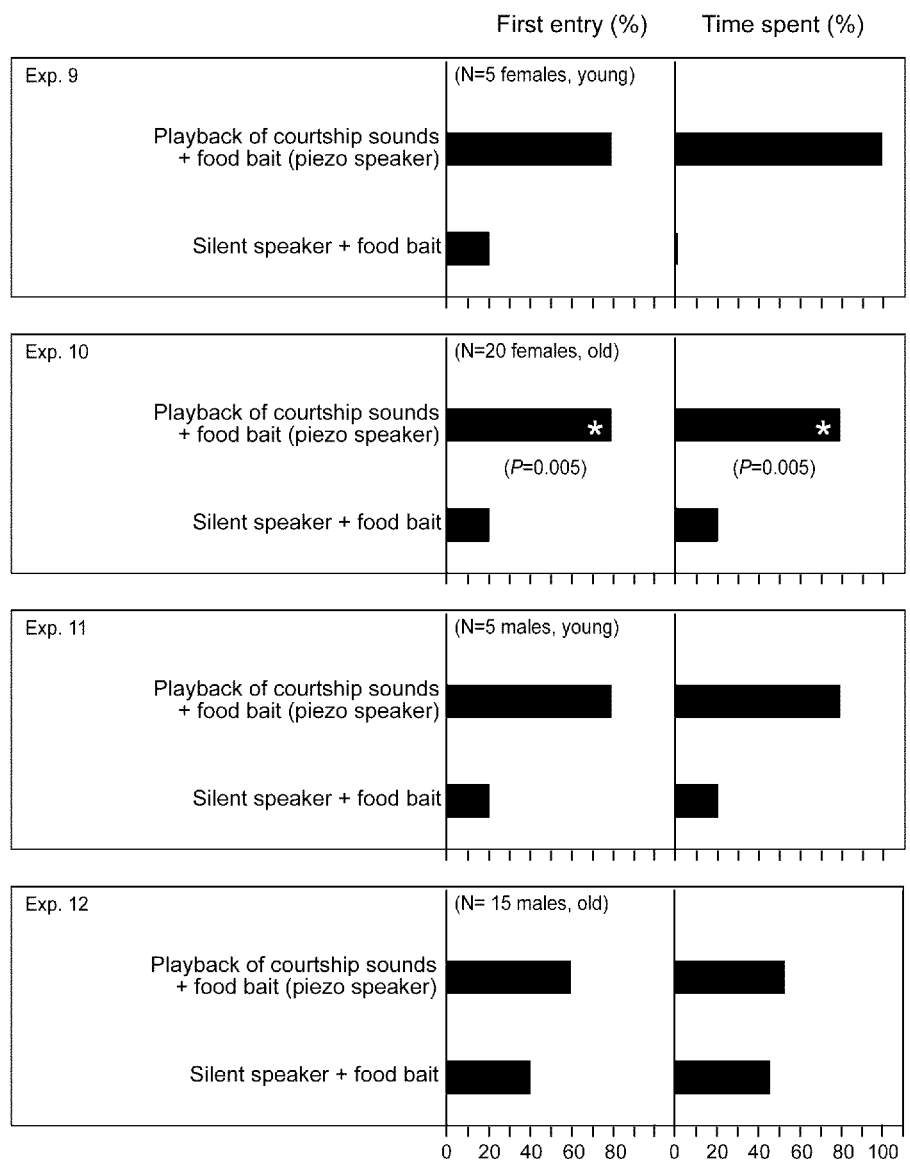

FIG. 10 illustrates the percentage of 20-wk-old adult female (Experiment 9), 11-month-old female (Experiment 10), 20-wk-old adult male (Experiment 11) and 11-month-old male (Experiment 12) *Rattus norvegicus* entering first a bait box (see FIG. 5) in response to playback recordings of vocalizations from courting male R. norvegicus (see FIG. 2) or in response to silence, and the percentage of time they spent in or around boxes with rat sound or silence First-choice and time-spent data were analyzed using a binominal test. In each set of paired bars, the bar with an asterisk (*) indicates a statistically significant preference (P<0.05) for a test stimulus.

Figure 11:
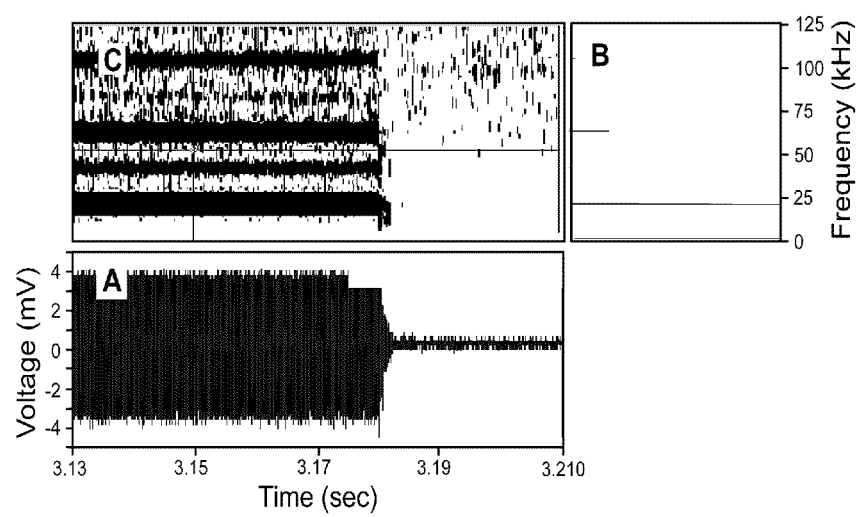

FIG. 11 illustrates the (A) waveform, (B) frequency and (C) time-frequency sound intensity (sonogram) of synthetic sound mimicking vocalizations from pups of *Rattus norvegicus*. Darker shades in C indicate more intense frequency components.

Figure 12:
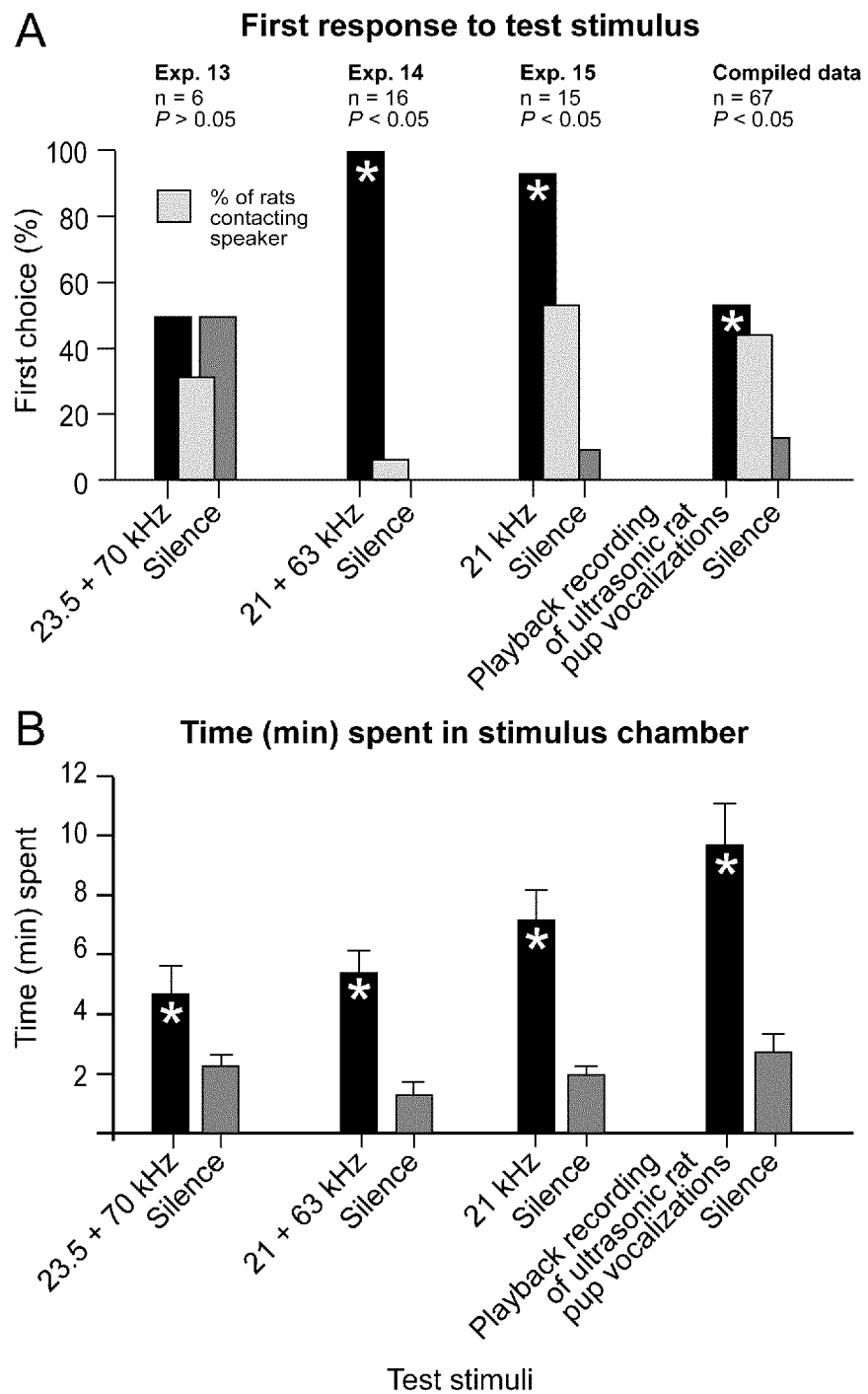

FIG. 12 illustrates (A) the first choice and (B) time spent in aquarium 4a or 4b (see FIG. 4) by adult male or female *Rattus norvegicus* in Experiments 13-15 in response to synthetic sound mimicking vocalizations from pups of *R. norvegicus* (see FIG. 11). "Compiled data" are gathered in Experiments 1-5. First-choice and time-spent data were analyzed using a binominal test and Student's t-test, respectively. In A or B of each experiment, bars with an asterisk (*) indicate a statistically significant preference (P<0.05) for a test stimulus.

Figure 13:
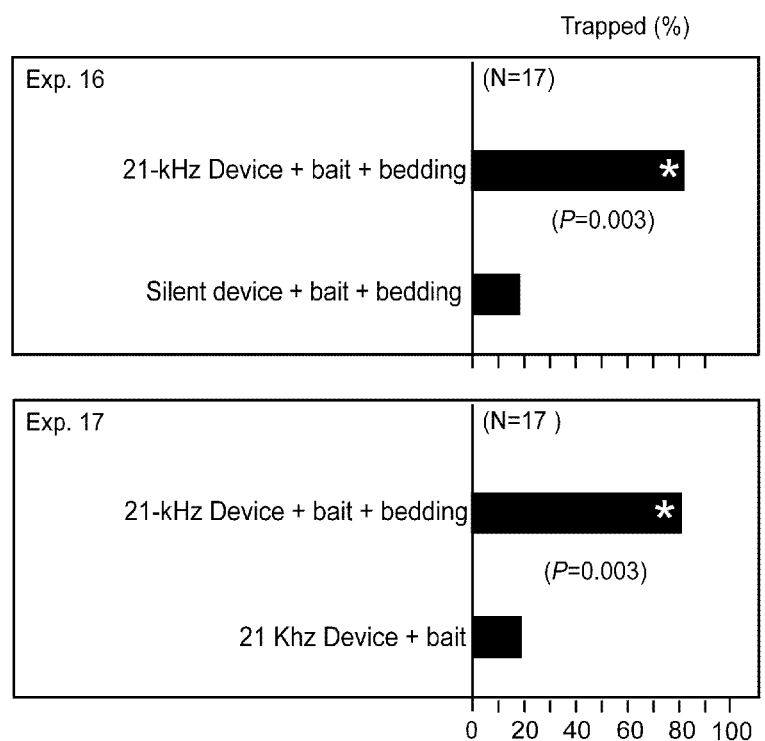

FIG. 13 illustrates the percentage of rats captured in Experiments 16 and 17 which tested the effects of 21-kHz rat pup sound (delivered by an electronic device) or rat bedding material (containing feces and urine odour of female rats) on captures of rats in paired bait boxes fitted with a food-baited snap trap. Both experiments were run on farms in the Lower Mainland of British Columbia. In each experiment, bars with an asterisk (*) indicate a statistically significant preference (P<0.05) for a test stimulus.

DETAILED DESCRIPTION OF THE INVENTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Some embodiments relate to acoustic signals comprising synthetic reproduction of sonic vocalizations (SVs) and/or ultrasonic vocalizations (USVs) by rats and mice for phonotactic attraction of rats, including juvenile, sub-adult and adult rats. The vocalizations may be of adult female mice, adult male rats, and/or rat pups. Some embodiments relate to acoustic signals comprising playback recordings of sonic vocalizations (SVs) and/or ultrasonic vocalizations (USVs) by rats and mice for phonotactic attraction of rats, including juvenile, sub-adult and adult rats. Other embodiments are directed to related methods of attracting rats using such acoustic signals, methods of making lures that use such acoustic signals for attracting rats, apparatus for generating such acoustic signals, and apparatus that use such acoustic signals for attracting rats.

Some embodiments relate to intensifying attraction and trapping efficacy by combining such acoustic signals with chemical stimuli to enhance the attraction of rats to a level higher than by responses to either sonic or chemical stimuli offered alone. Some embodiments relate to the deployment of such signals alone or in combination with chemical stimuli for attracting and capturing rats, including juvenile, sub-adult and adult rats, in any type of trapping device, or for exposing them to a rodenticide such as a toxicant or chemosterilant.

According to some embodiments, the chemical stimulus may be a composition as described in WO/2013/003946 entitled "Compositions And Methods For Attracting And Stimulating Feeding By Mice And Rats", incorporated herein by reference in its entirety.

According to some embodiments, the chemical stimulus may be one or more compounds derived from urine or feces of female rats, for example from bedding material used by female rats.

According to some embodiments. the chemical stimulus may be a cereal-based composition as set out in U.S. provisional application No. 61/826,432, for example a composition comprising a cereal flour, a cereal bran, a gelling agent, a sugar, an oil, an emulsifier and a humectant. The cereal flour may be oat flour, rice flour, wheat flour, spelt flour, barley flour, rye flour, soybean flour, and/or corn flour. According to an example embodiment, the cereal flour is a mixture of oat flour and rice flour. In such embodiments, the composition may comprise oat flour at 10-20% by weight, and rice flour at 5.0-15% by weight. The cereal bran may be oat bran, rice bran, wheat bran, spelt bran, barley bran, rye bran, soybean bran, and/or corn bran. According to an example embodiment, the cereal bran is wheat bran flour. In some embodiments, the composition may comprise the cereal bran at 1.0-10% by weight. According to some embodiments, the gelling agent may be agar, gelatin, pectin, guar, carob, locust bean, starch and/or modified starches. According to an example embodiment, the gelling agent is gelatin or agar. In some embodiments, the composition may comprise the gelling agent at 0.1 to 5.0% by weight. According to some embodiments, the sugar may be a monosaccharide (e.g. fructose, glucose, galactose, xylose, ribose) or a disaccharide (e.g. sucrose, lactose, maltose). According to an example embodiment, the sugar is fructose. In some embodiments, the composition may comprise the sugar at 0.1-5.0% by weight. According to some embodiments, the oil may be a vegetable oil (e.g. safflower oil, soybean oil, cottonseed oil, canola oil, sunflower oil, hempseed oil, olive oil, rapeseed oil, corn oil) or a fish oil (e.g. salmon oil, cod liver oil, herring oil, sardine oil, mackerel oil). According to an example embodiment, the oil is a fish oil, in particular salmon oil. In some embodiments, the composition may comprise the oil at 0.01 to 1.0% by weight. According to some embodiments, the emulsifier may be a lecithin, monoglyceride, diglyceride, monostearate, polystearate, and/or propylene glycol ester. According to an example embodiment, the emulsifier is soy lecithin. In some embodiments, the composition may comprise the emulsifier at 0.01 to 1.0% by weight. According to some embodiments, the humectant may be carrageenan gum, carboxymethyl cellulose, polyacrylic acid and/or xanthan gum. According to an example embodiment, the humectant is carrageenan gum powder. According to some embodiments, the composition may also comprise a preservative, dimethyltrisulfide, and/or one or more compounds derived from bedding contaminated by female mice and/or rats. According to some embodiments, the composition may include one or more or all of the six attractive semiochemicals described in WO/2013/003946, namely 2-hydroxy-3-methylcyclopent-2-en-1-one, butyric acid, 2,3-butadione, 3-methylbutanal, 5-methyl-(E)-2-hepten-4-one and γ-octalactone. According to some embodiments, the composition may be heat treated by, for example, mixing one or more components of the composition (e.g. the gelling agent, preservative and/or the humectant) with hot water (e.g. boiling hot water) and then combining with the remaining components. In some embodiments the heat treated composition may be combined with a rodenticide. As demonstrated in U.S. provisional application No. 61/826,432, the cereal based composition described herein showed efficacy in attracting and stimulating feeding in rats in both laboratory and field tests.

EXAMPLE 1

Recordings of Sonic and Ultrasonic Vocalizations

Seven 3-day-old rat pups, *Rattus norvegicus,* were removed from their natal nest and placed separately into a tissue paper-lined aquarium (30×30×60 cm). Sonic and ultrasonic vocalizations of each pup were digitally and simultaneously recorded using microphones positioned 3 cm above the pup. Recordings commenced immediately upon placement of a pup and continued for up to 3 h (1 h on average). Following recordings, pups were returned to their natal nest and mother.

Three pairs of a 9-week-old virgin male and female rats, *Rattus norvegicus,* were placed separately in a cage (54.5× 39.5×20.0 cm) with a removable galvanised steel mesh (mesh size: 2.5 cm) dividing the cage into two equal compartments. This design prevented mating but allowed visual, olfactory, acoustic and limited tactile interactions between the male and female rats. Their sonic and ultrasonic vocalizations were digitally and simultaneously recorded using microphones positioned 21 cm above the centre of the cage floor with or without the barrier in place. Concurrent video recordings allowed the investigators to relate vocalizations to specific behaviour. Recordings commenced immediately upon placement of a pair into the cage and continued for up to 1 h (30 min on average) after the barrier was removed.

Vocalizations from caged protective nursing female mice were recorded in situ with the microphones placed 5 cm above the nest.

Vocalizations in the sonic range (0-24 kHz) were recorded using an AKG CK 61-ULS condenser microphone (AKG Acoustics, Nashville, Tenn., USA). The sound-to-noise ratio was improved by pre-amplifying [SC-2040 amplifier, National Instruments (NI), Austin, Tex., USA] sounds prior to digitizing via a data acquisition (DAQ) card. Vocalizations in the ultrasonic range (20-100 kHz) were recorded using a "Mini" SiSonicTM Ultrasonic Acoustic Sensor (SPM0404UD5 Knowles®, Itasca Ill. 60143, peak frequency response: 10-65 kHz). Recordings were saved to a desktop computer (Dell, Round Rock, Tex., USA) equipped with a 16 bit DAQ (NI PCIe-6259) and programmed with LabVIEW 7.1 (NI). The sound-to-noise ratio was improved by pre-amplifying sounds prior to digitizing at 250 kHz per channel via the DAQ card. Recorded sounds were analyzed for duration, frequency, intermittency and relative intensity using LabView's Joint Time Frequency Analyzer.

Vocalizations of rat pups contained frequency components in the sonic range (1.8-7.5 kHz) and ultrasonic range (21-24 kHz, 40-50 kHz and 60-96 kHz) (FIG. 1). Dominant frequencies occurred in the sonic or ultrasonic range depending on the frequency response of the respective microphone. These results indicate that the SVs and USVs emissions from rat pups are considerably and unexpectedly more complex than those recorded by Uematsu et al. (2007), who recorded emissions only in the 40-50 kHz ultrasonic range.

Figure 3:
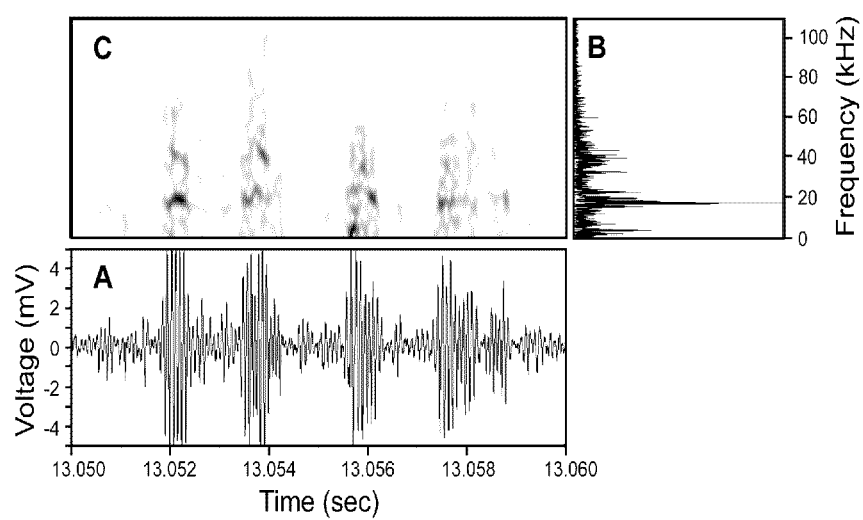
FIG. 3 illustrates the analysis of waveform (A), frequency (B) and time-frequency sound intensity (sonogram) (C) of a sound produced by a nursing protective female house mouse, *Mus musculus*. The darker shades in C indicate more intense frequency components.

Unexpectedly, vocalizations by courting adult male rats contained many complex vocalizations (FIG. 2) with frequency components in the sonic range (1.5-20 kHz) and ultrasonic range (20-100 kHz), Vocalizations from a protective nursing female mouse contained frequency components in the sonic range (8-12 kHz) and ultrasonic range (25-100 kHz) (FIG. 3).

The vocalizations embodied in FIGS. 1-3 are more complex than ever before recorded. They suggest that employing the full complexity of vocalizations in playback recordings or synthesized sonic and ultrasonic signals will be required to achieve optimal practical utility of sonic and ultrasonic signals used to manage rodent pests.

EXAMPLE 2

Playback of Vocalizations

Selected vocalizations of pups were compiled in a single file that was looped (automatically rerun) and played back for the duration of each bioassay using equipment described above. The playback recording was emitted through a piezoelectric speaker with a resonance frequency of 0.06 kHz (Buzzer piezo element: CEB-44D06, Digi-Key, Thief River Falls, Minn., USA) or a Sennheiser 70 headphone speaker (frequency response: 10 to 39,500 Hz, 0.05% THD; Sennheiser Electronic Co., Old Lyme, Conn., USA).

EXAMPLE 3

Behavioral Experiments Involving Play-Back of Recorded Rat Pup Sound

Behavioral responses of (i) >12-week-old reproductively active adult male and female rats, (ii) 6- to 8-week-old sub-adult male and female rats, and (iii) 4- to 6-week-old juvenile rats to playback recordings of rat pup vocalizations were tested in T-tube experiments (FIG. 4). The experimental set-up consisted of 3 glass aquaria (30×30×60 cm each) interconnected by a T-tube (75×50 cm; 10 cm diameter), and it was housed in a beige enclosure (3×2×1.3 m) with a small observation port. Prior to experiments, rats were deprived of food but not water for 16 h. For each replicate, a single rat was placed into aquarium 1 which was illuminated by a 20-W red bulb to facilitate observations of the rat's position. Following 1 h of acclimation, the aluminum gate 2 was opened, allowing the rat to enter the stem of the T-tube 3 in response to randomly assigned silence or sonic stimuli emitted from a piezoelectric speaker 5a with a resonance frequency of 0.06 kHz (Buzzer piezo element: CEB-44D06, Digi-Key, Thief River Falls, Minn., USA) or a Sennheiser 70 headphone speaker 5b, frequency response: 10 to 39,500 Hz, 0.05% THD; Sennheiser Electronic Co., Old Lyme, Conn., USA) in the inner upper corner of aquaria 4a or 4b.

A rat was classed a responder if it entered with all four paws aquaria 4a or 4b. Both a rat's first response and position at each of 30 one-min intervals were recorded. The latter criterion was correlated with the time a rat spent in aquaria 4a or 4b. Between each replicate, aquaria were cleaned with a dish soap detergent and wiped with a commercial pet urine odor remover (Nature's Miracle®, Eight in One Pet Products, Haupauge, N.Y., USA). The T-Tube was cleaned with Sparkleen and baked at 200° C. for 20 min. First-choice and time-spent data were analyzed using binomial and Students t-tests, respectively.

In Experiments 1 and 2, significantly more adult male and female rats preferred as a first choice, and spent most time in, the aquarium associated with playback recordings of rat pup vocalizations (FIG. 6). In Experiments 3 and 4, significantly more sub-adult males, but not sub-adult females, preferred as a first choice the aquarium associated with playback recordings of rat pup vocalizations (FIG. 7). In Experiments 3 and 4, both sub-adult males and females spent significantly more time in the aquarium associated with the playback recording of rat pup vocalizations than in the aquarium associated with a silent control. In Experiment 5, significantly more juvenile rats preferred as a first choice, and spent most time in, the aquarium associated with playback recordings of rat pup vocalizations (FIG. 8).

In Experiment 6 which tested the sonic portion (0-20 KHz) of the pup's vocalizations as the treatment stimulus, all rats (n=8) preferred as a first choice the aquarium associated with the treatment stimulus over the aquarium associated with the silent control stimulus.

These results suggest that sonic and ultrasonic signals emitted by rat pups would have practical utility if they were delivered from a device placed in or near a trap or in a location where the attracted rat was exposed to a rodenticide, e.g. a toxicant or a chemosterilant.

EXAMPLE 4

Behavioral Experiments Involving Play-Back of Recorded Vocalizations of a Protective Nursing Female Mouse With Litter Behavioral responses of >12-week-old, reproductively active adult male and female rats, to playback recordings of a protective nursing female house mouse, *Mus musculus* (FIG. 3) were tested in a circular, galvanised steel arena (75 cm high×2 m diameter; see FIG. 5) illuminated by a 20-W red bulb to facilitate observations. For each replicate, a single rat was transferred from a holding cage to the arena in a covered stainless steel bowl, which was placed equidistant from the bait boxes, each provisioned with a 1-g food bait. Following 5 min of acclimation, the cardboard cover on the bowl was removed, allowing the rat to exit and to respond to test stimuli randomly assigned to bait boxes. Sonic stimuli were emitted from a piezoelectric speaker as in Example 3.

A rat was classed a responder if it entered with all four paws bait box 2a or 2b. Between each replicate, the arena and bait boxes were cleaned with a dish soap detergent and wiped with a commercial pet urine odor remover (Nature's Miracle®, Eight in One Pet Products, Haupauge, N.Y., USA). First-choice and time-spent data were analyzed using Chi-square tests with Yates correction and Students t-tests.

In Experiments 7 and 8, significantly more adult male rats and most adult female rats entered first the bait box with the sound stimulus (FIG. 9).

These results suggest that sonic and ultrasonic signals emitted by adult female mice would have practical utility if they were delivered from a device placed in or near a trap or in a location where the attracted rat was exposed to a rodenticide, e.g. a toxicant or a chemosterilant.

EXAMPLE 5

Behavioral Experiments Involving Played-Back Sound Recorded from Courting Adult Male Rats in Combination With a Chemical Stimulus The inventors have previously demonstrated in U.S. provisional application No. 61/826,432 superior attraction of rats to a chemical bait that included the following components: agar (or gelatin), water, oat flour, rice flour, wheat bran, fructose, soy lecithin, salmon oil, carrageenan gum powder, 2-hydroxy-3-methylcyclopent-2-en-1-one, butyric acid, 2,3-butadione, 3-methylbutanal, 5-methyl-(E)-2-hepten-4-one, γ-octalactone and dimethyltrisulfide. Experiments 9-13 tested whether a sonic stimulus could be used to improve the attractiveness by combining sonic and food bait stimuli.

Behavioral responses of young (20-week-old) and old (11-month-old) male and female rats to playback recordings of courting adult male rats were tested in arena Experiments 9-12. The experimental procedure was equivalent to that described in Example 4.

A rat was classed a responder if it entered with all four paws bait box 2a or 2b. Both a rat's first response and position at each of 30 one-min intervals were recorded. The latter criterion was correlated with the time a rat spent in and around bait box 2a or 2b. Between each replicate, the arena was cleaned as described for Example 4. First-choice and time-spent data were analyzed using Chi-square tests with Yates correction and Students t-tests.

In Experiment 9, young female rats entered most often first the bait box with both the sound and chemical bait stimuli (FIG. 10). Young females also spent more time in or around the "sound" box than the silent box.

In Experiment 10, significantly more old females entered first the bait box with the sound stimulus (FIG. 10). Old Females also spent significantly more time in or around the sound box than the silent box.

In Experiment 11, young males entered most often first the bait box with the sound stimulus (FIG. 10). Young males also spent more time in or around the sound box than the silent box.

In Experiment 12, old males equally often entered first bait boxes with or without the sound stimulus (FIG. 10). They also spent equal amounts of time in or around boxes with or without sound.

These results suggest that sonic and ultrasonic signals emitted by courting adult male rats, as well as sonic stimuli from rat pups and adult female mice, would have enhanced practical utility if they were delivered along with a chemical stimulus from a device placed in or near a trap or in a location where the attracted rat was exposed to a rodenticide, e.g. a toxicant or a chemosterilant.

EXAMPLE 6

Synthesis of Rat Pup Sound

Vocalizations were synthesized using a Dell desktop computer equipped with a 16 bit DAQ card (NI PCIe-6259) and programmed with LabVIEW 8.6 (NI). A custom program (algorithm) designed to drive the production of synthetic SVs and USVs generated by the circuit board, to modulate the frequency (Hz), duration, and intensity of amplified synthetic SVs and USVs, and to alter the intermittent silence between SVs and USVs, was developed and used to produce synthetic rat pup sounds (FIG. 11) consistent with rat pup vocalizations previously recorded (FIG. 1). The program generated one of 23.5- and 70-, 21- and 63-. or 21-k cycles per sec sinusoidal wave with a random duration ranging between 30 and 300 msec. Intermittent silent intervals had a randomly assigned duration of 0.4 to 5 sec. The intensity of synthetic sound was consistent with vocalizations from pups of *R. norvegicus*.

EXAMPLE 7

Development of a Battery-Powered Electronic Device Mimicking Rat Pup Sounds

The inventors developed an independent electronic device to run the same program with equivalent sound-producing qualities as described in EXAMPLE 6. The device was programmed to produce 22±3-k cycles per sec sine waves mimicking the range, duration, and intermittency of rat pup vocalizations.

The success in synthesizing rat pup vocalizations using a custom program (algorithm) as embodied in EXAMPLES 6 and 7 indicates that vocalizations emitted by adult male rats or adult female mice could also be synthesized using similar algorithms.

EXAMPLE 8

Behavioral Experiments Involving Synthetic Rat Pup Sounds

Behavioral responses of male and female *R. norvegicus* to various types of synthetic sound stimuli or to silent control stimuli were tested in two-choice T-tube experiments (see FIG. 4 and EXAMPLE 3). In Experiments 14 and 15, but not in Experiment 13, significantly more rats preferred as a first choice the aquarium associated with synthetic sound mimicking vocalizations from pups of *R. norvegicus* (FIG. 11). In each of Experiments 13-15, significantly more Norway rats spent more time in the aquarium associated with the synthetic sound stimulus than in the aquarium associated with the silent control stimulus. The percentage of rats contacting the speaker in Experiment 15, which tested the synthetic rat pup sound as illustrated in FIG. 11, compared well with the percentage of rats contacting the speaker in Experiments 1-5 ("compiled data"), which tested playback recordings of rat pup vocalizations (see FIG. 1).

The positive behavioral response of both male and female Norway rats to synthetic rat pup vocalizations indicate that such synthetic vocalizations could have practical utility if they were delivered from a device placed in or near a trap or in a location where the attracted rat was exposed to a rodenticide, e.g. a toxicant or a chemosterilant. Moreover, it is also indicated that synthetic vocalizations from adult male rats and adult female mice would have similar practical utility.

EXAMPLE 9

Field Experiments Testing the Effects of an Electronic Device Mimicking Rat Pup Sounds in Combination With a Chemical Stimulus Field Experiments 16 and 17 were designed to test the interactive effects of combining synthetic rat pup sound with a chemical food bait alone or with rat bedding material (contaminated with the odor of feces and urine odor of female rats) removed after six days from laboratory cages containing female Norway rats. The chemical food bait was identical to the bait described in EXAMPLE 5.

Both experiments were run on farms in the Lower Mainland of British Columbia. Each experiment deployed 3-4 pairs of bait boxes, with 50 cm between boxes in each pair, and >5 m between pairs. All boxes were fitted with a food-baited snap trap and were placed along the walls of a barn wherever possible. Trap catch data were analyzed using Chi-square test with Yates correction.

Experiment 16 tested the effect of a battery-powered, electronic device emitting synthetic rat pup sounds (see EXAMPLE 7) in combination with the food bait and contaminated bedding, compared to the food bait and bedding alone.

Experiment 17 compared catches in traps baited with a battery-powered, electronic device emitting synthetic rat pup sounds (see EXAMPLE 7) in combination with the food bait and contaminated bedding, compared to catches in traps containing the sound-emitting device and the food bait.

In Experiment 16, significantly more rats were captured in boxes fitted with the rat pup sound-emitting electronic device in combination with the two chemical stimuli than in boxes with just the chemical stimuli (FIG. 13).

In Experiment 17, significantly more rats were captured in boxes fitted with the rat pup sound-emitting electronic device in combination with the two chemical stimuli than in trap boxes fitted with the sound-emitting device and the food bait (FIG. 13).

These results indicate that adding the odor of bedding contaminated by female feces and urine enhances the catch over that achieved with the synthetic sonic and ultrasonic vocalizations in combination with the food bait. Thus a complex composition comprising synthetic sonic and ultrasonic vocalizations from rats or mice with different types of attractive chemical stimuli should improve the utility of using these attractive stimuli to attract rats to a trap, a box containing a trap or a location where the attracted rats would be exposed to a rodenticide, e.g. a toxicant or a chemosterilant.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed:

1. An acoustic signal for attracting rats comprising a playback recording or synthetic generation of multi-frequency vocalizations of rats or mice, wherein the acoustic signal has a modulated duration and intensity and comprises a first frequency component and a second frequency component different from the first frequency component.

2. An acoustic signal according to claim 1, further comprising one or more sonic frequency components in the range of 1.8-7.5 kHz and/or one or more ultrasonic frequency components in the ranges of 21-24 kHz, 40-50 kHz and/or 60-96 kHz.

3. An acoustic signal according to claim 1, further comprising one or more sonic frequency components in the range of 15-20 kHz and/or one or more ultrasonic frequency components in the range of 20-100 kHz.

4. An acoustic signal according to claim 1, further comprising one or more sonic frequency components in the range of 8-12 kHz and/or one or more ultrasonic frequency components in the range of 25-100 kHz.

5. An acoustic signal according to claim 1, wherein the vocalizing species of rat is selected from the group consisting of *Rattus norvegicus, Rattus rattus, Rattus annandalei, Rattus enganus, Rattus everetti, Rattus exulans, Rattus hainaldi, Rattus hoogerwerfi, Rattus korinchi, Rattus macleari, Rattus montanus, Rattus morotaiensis, Rattus nativitatis, Rattus ranjiniae, Rattus sanila, Rattus stoicus, Rattus timorensis, Rattus nitidus, Rattus pyctoris, Rattus turkestanicus, Rattus adustus, Rattus andamanensis, Rattus argentiventer, Rattus baluensis, Rattus blangorum, Rattus burrus, Rattus hoffmanni, Rattus koopmani, Rattus losea, Rattus lugens, Rattus mindorensis, Rattus mollicomulus, Rattus osgoodi, Rattus palmarum, Rattus rattus, Rattus satarae, Rattus simalurensis, Rattus tanezumi, Rattus tawitawiensis, Rattus tiomanicus, Rattus bontanus, Rattus foramineus, Rattus marmosurus, Rattus pelurus, Rattus salocco, Rattus xanthurus, Rattus arfakiensis, Rattus arrogans, Rattus elaphinus, Rattus feliceus, Rattus giluwensis, Rattus jobiensis, Rattus leucopus, Rattus mordax, Rattus niobe, Rattus novaeguineae, Rattus omichlodes, Rattus pococki, Rattus praetor, Rattus richardsoni, Rattus steini, Rattus vandeuseni, Rattus verecundus, Rattus colletti, Rattus fuscipes, Rattus lutreolus, Rattus sordidus, Rattus tunneyi,* and *Rattus villosissimus.*

6. An acoustic signal according to claim 1, wherein the vocalizing species of mice is *Mus musculus.*

7. A method of attracting rats comprising:
  (a) placing a device capable of producing acoustic signals in an area determined to have a need for capturing and/or killing rats; and
  (b) causing the device to emit the acoustic signal according to claim 1, wherein the device comprises a processor programmed to generate the acoustic signal.

8. A method according to claim 7 wherein the processor comprises an electronically activatable microchip.

9. A method according to claim 7, wherein in step (a) the device is contained in, placed adjacent to, or integrated with a trap that captures attracted rats.

10. A method according to claim 7, wherein in step (a) comprises placing the device in an area where attracted rats will be exposed to a rodenticide.

11. A method according to claim 7, wherein step (b) comprises modulating one or more of the frequency, duration and intensity of the acoustic signal.

12. A method according to claim 7, wherein step (b) comprises providing intermittent silences between the acoustic signals.

13. A method according to claim 12, wherein step (b) comprises altering durations of the intermittent silences.

14. A method according to claim 7, wherein step (a) further comprises placing in the area a chemical stimulus to enhance the attraction of rats.

15. A method according to claim 14, wherein the chemical stimulus comprises one or more stimuli selected from the group consisting of 2-hydroxy-3-methylcyclopent-2-en-1-one, butyric acid, 2,3-butadione, 3-methylbutanal, 5-ethyl-(E)-2-hepten-4-one, γ- octalactone, 4-hydroxy-2,5-dimethylfuran-3-one, 6-methyl-4-heptanone, dimethyltrisulfide, nonanoic acid, decanoic (capric) acid, dodecanoic (lauric) acid, tetradecanoic (myristic) acid, hexadecanoic (palmitic) acid, (Z)-octadec-9-enoic (oleic) acid, octadecanoic (stearic) acid, lactic acid, glycerol, lard and cracklings, oat flour, rice flour, wheat bran, fructose, soy lecithin, safflower oil, salmon oil, and compounds derived from bedding contaminated by the urine and feces of female mice and/or rats.

16. A method according to claim 14, wherein the chemical stimulus comprises 2- hydroxy-3-methylcyclopent-2-en-1-one, butyric acid, 2,3-butadione, 3-methylbutanal, 5-methyl-(E)-2-hepten-4-one, and γ-octalactone.

17. An apparatus for attracting rats comprising a processor programmed to generate the acoustic signal according to claim 1.

18. An apparatus according to claim 17, wherein the processor comprises an electronically activatable microchip.

19. An apparatus according to claim 17, further comprising:
an amplifier for amplifying the acoustic signal; and
a speaker for emitting the amplified acoustic signal.

20. A system including the apparatus of claim 17, wherein the apparatus is contained in, placed adjacent to, or integrated with a trap capable of capturing or killing an attracted rat.

* * * * *